United States Patent
Bochmann et al.

(10) Patent No.: US 6,762,258 B2
(45) Date of Patent: Jul. 13, 2004

(54) METAL COMPLEXES AS CATALYST COMPONENT FOR OLEFIN POLYMERIZATION

(75) Inventors: Manfred Bochmann, Norwich (GB); Mark John Sarsfield, Manchester (GB)

(73) Assignee: BP Chemicals Limited, London (GB)

( * ) Notice: Subject to any disclaimer, the term of this patent is extended or adjusted under 35 U.S.C. 154(b) by 49 days.

(21) Appl. No.: 09/924,603

(22) Filed: Aug. 9, 2001

(65) Prior Publication Data

US 2002/0058762 A1 May 16, 2002

Related U.S. Application Data

(63) Continuation of application No. PCT/GB99/04350, filed on Dec. 22, 1999.

(30) Foreign Application Priority Data

Feb. 9, 1999 (GB) .............................. 9902697

(51) Int. Cl.$^7$ .......................... C08F 4/68; C08F 4/695; C08F 4/70
(52) U.S. Cl. .................. 526/161; 526/113; 526/114; 526/115; 526/129; 526/134; 526/169.1; 526/171; 526/172; 502/103; 502/117; 502/118; 502/120; 502/150; 502/155; 502/162; 502/167
(58) Field of Search .................. 526/161, 172, 526/113, 114, 115, 169.1, 171; 502/117, 167, 155, 162

(56) References Cited

U.S. PATENT DOCUMENTS 6,133,387 A * 10/2000 Xu et al. ..................... 526/172
6,239,237 B1 * 5/2001 Xu et al. ..................... 526/161

FOREIGN PATENT DOCUMENTS

WO    WO 98/30609    7/1998

OTHER PUBLICATIONS

M. Witt, et al., "Synthesis and Structural Characterization of P–Functionalized Metallacyclophosphazenes", Chemical Abstracts, 127:116633d, Columbus, Ohio, US, vol. 127, No. 8, p. 1273 (1997).

M. W. Avis et al., "Reactions of bis(iminophosphoranes with palladium(II) dichloride: metal–induced tautomerization orthopalladation and unexpected platinum–assisted [2 + 2] cycloaddition of an aryl–nitrile, with a phosphinimine moiety", Journal of Organometallic Chemistry 527, pp. 263–276, (1997).

M. Rietzel, et al., "Formation of Spirocyclic Imidophosphinato Complexes: Crystal Structures of [V(OPPh$_2$NPPh$_2$O)$_2$O] and [Mo(NPPh$_2$NPPh$_2$O)$_2$Cl$_2$]", J. Chem. Soc. Dalton Trans., pp. 1285–1290, (1991).

H. W. Roesky, et al., "A Volatile Cyclic Metallaphosphazene; Preparation and X–Ray Structure of [(CF$_3$)$_2$PN]$_2$NVCl$_2$", J. Chem. Soc., Chem. Commun., pp., 366–367, (1989).

* cited by examiner

*Primary Examiner*—Roberto Rabago
(74) *Attorney, Agent, or Firm*—Finnegan, Henderson, Farabow, Garrett and Dunner, L.L.P.

(57) ABSTRACT

Novel nitrogen containing transition metal complexes have general formula (I): wherein M is Fe[II], Fe[III], Ni[II], Co[I], Co[II], Co[III], V[III], Mn[I], Mn[II], Mn[III], Mn[IV], Ru[II], Ru[III] or Ru[IV]; Pd[II], V[III], V[IV] or V[V]. X represents an atom or group covalently or ionically bonded to the transition metal M; R is independently selected from hydrogen, halogen, hydrocarbyl, substituted hydrocarbyl, heterohydrocarbyl or substituted heterohydrocarbyl; Z is a bridging group comprising a donor atom of N, P or S or alternatively is a neutral group comprising a C$_1$–C$_4$ alkylene group, a silyl or germyl group, and n= an integer to satisfy the valency of M. The complexes are suitable for use on the polymerization and copolymerization of olefins (I)

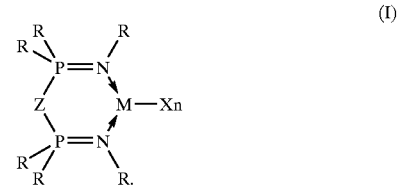

40 Claims, 1 Drawing Sheet

Fig. 1

METAL COMPLEXES AS CATALYST COMPONENT FOR OLEFIN POLYMERIZATION

This application is a continuation of international application No. PCT/GB99/04350 filed Dec. 22, 1999.

BACKGROUND OF THE INVENTION

The present invention relates to transition metal complex compounds, to polymerisation catalysts based thereon and to their use in the polymerisation and copolymerisation of olefins.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polymerisation of ethylene. Such polymers and copolymers are used extensively in the manufacture of flexible blown film.

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

Patent Application WO98/27124 published on Jun. 25, 1998 discloses that ethylene may be polymerised by contacting it with certain iron or cobalt complexes of selected 2,6-pyridinecarboxaldehydebis(imines) and 2,6-diacylpyridinebis(imines).

An object of the present invention is to provide a novel catalyst suitable for polymerising monomers, for example, olefins, and especially for polymerising ethylene alone or for copolymerising ethylene with higher 1-olefins. A further object of the invention is to provide an improved process for the polymerisation of olefins, especially of ethylene alone or the copolymerisation of ethylene with higher 1-olefins to provide homopolymers and copolymers having controllable molecular weights. For example, using the catalysts of the present invention there can be made a wide variety of polyolefins such as, for example, liquid polyolefins, oligomers, linear alpha-olefins, resinous or tacky polyolefins, solid polyolefins suitable for making flexible film and solid polyolefins having high stiffness.

SUMMARY OF THE INVENTION

The present invention provide nitrogen containing transition metal complexes having the following Formula.

FORMULA I wherein

M is Fe[II], Fe[III], Ni[II], Co[I], Co[II], Co[III], V[III], Mn[I], Mn[II], Mn[III], Mn[IV], Ru[II], Ru[III] or Ru[IV]; Pd[II], V[III], V[IV] or V[V].

X represents an atom or group covalently or ionically bonded to the transition metal M;

R is independently selected from hydrogen, halogen, hydrocarbyl, substituted hydrocarbyl, heterohydrocarbyl or substituted heterohydrocarbyl;

Z is a bridging group comprising a donor atom of N, P or S or alternatively is a neutral group comprising a $C_1$–$C_4$ alkylene group, a silyl or germyl group, and n=an integer to satisfy the valency of M.

DETAILED DESCRIPTION OF THE INVENTION

The preferred bridging group Z is —$CH_2$— or a donor atom of N preferably pyridyl.

In the preferred complexes the general formula may be represented by wherein M, Z, X and n are as defined above and wherein $R^1-R^{14}$ are independently selected from hydrogen, halogen, hydrocarbyl, substituted hydrocarbyl, heterohydrocarbyl, or substituted heterohydrocarbyl.

Preferably at least one of $R^1-R^{10}$ contains two or more carbon atoms and is preferably isopropyl and any two or more or $R^{11}-R^{14}$ are hydrocarbyl or aryl substitutents.

The most preferred groups $R^{11}-R^{14}$ are phenyl, alkyl or cycloalkyl eg. cyclohexyl.

In the most preferred complexes the general formula may be represented by wherein R is hydrogen, hydrocarbyl. The preferred metal atoms M in each of the above formulae are Fe, Ni or Co.

Each of the nitrogen atoms is coordinated to the transition metal M by a "dative" bond, ie a bond formed by donation of a lone pair of electrons from the nitrogen atom. The remaining bonds on each nitrogen atom are covalent bonds formed by electron sharing between the nitrogen atoms and the organic ligand as shown in the defined formula for the transition metal complex illustrated above.

The atom or group represented by X in the compounds of the above Formulae can be, for example, selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl. Examples of such atoms or groups are chloride; bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X in the compounds of Formula I are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl or a chelating group eg. acetylacetonate. Chloride is particularly preferred.

The present invention further provides a polymerisation catalyst comprising (1) a nitrogen-containing transition metal compound having the Formula I as hereinbefore defined, and (2) an activating quantity of an activator compound.

The activator compound for the catalyst of the present invention is suitably selected from organoaluminium compounds and boron compounds. Suitable organoaluminium compounds include trialkyaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable boron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerize small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe, Co, Mn or Ru metal atom in the compound of Formula I.

A further aspect of the present invention provides a polymerisation catalyst system comprising (1) as the transition metal compound, a compound having the Formula I (2) an activating quantity of an activator compound selected from organoaluminium and hydrocarbylboron compounds and optionally (3) a neutral Lewis base.

In this further aspect of the present invention, the iron and cobalt compounds are preferred. The preferences in relation to the activator compound are the same as expressed above in relation to the catalyst of the present invention. Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitrites, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures eg up to 120° C. can be carried out if desired, eg to achieve better mixing of the components. It is preferred to carry out the bringing together of components (1), (2) and (3) in an inert atmosphere (eg dry nitrogen) or in vacuo. If it is desired to use the catalyst on a support material (see below), this can be achieved, for example, by preforming the catalyst system comprising components (1), (2) and (3) and impregnating the support material preferably with a solution thereof, or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The catalysts of the present invention can if desired comprise more than one of the defined transition metal compounds.

In addition to said one or more defined transition metal compounds, the catalysts of the present intention can also include one or more other types of transition metal compounds or catalysts, for example, other nitrogen containing Fe or Co catalysts such as those described in our copending application PCT/GB98/02638. Examples of such other catalysts include 2,6-diacetylpyridinebis(2,4,6 trimethyl anil) $FeCl_2$.

The catalysts of the present invention can also include one or more other transition metal compounds, such as those of the type used in conventional Ziegler-Natta catalyst systems, metallocene-based catalysts, monocyclopentadienyl- or constrained geometry based catalysts, or heat activated supported chromium oxide catalysts (eg Phillips-type catalyst).

The catalysts of the present invention can be unsupported or supported on a support material, for example, silica, alumina, or zirconia, or on a polymer or prepolymer, for example polyethylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, comprising contacting the monomeric olefin under polymerisation conditions with the polymerisation catalyst or catalyst system of the present invention.

A preferred process comprises the steps of:
a) preparing a prepolymer-based catalyst by contacting one or more 1-olefins with a catalyst system, and
b) contacting the prepolymer-based catalyst with one or more 1-olefins, wherein the catalyst system is as defined above.

The present invention also encompasses as another aspect the use of a complex as defined above as a catalyst for the polymerisation of 1-olefins.

In the text hereinbelow, the term "catalyst" is intended to include "catalyst system" as defined previously and also "prepolymer-based catalyst" as defined above.

The polymerisation conditions can be, for example, solution phase, slurry phase, gas phase or bulk phase, with polymerisation temperatures ranging from −100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are, for example, ethylene and $C_{2-20}$ α-olefins, specifically propylene, 1-butene, 1-pentene, 1-hexene, 4-methylpentene-1,1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene.

Preferred monomers for homopolymerisation processes are ethylene and propylene.

The catalysts and process of the invention can also be used for copolymerising ethylene or propylene with each other or with other 1-olefins such as 1-butene, 1-hexene, 4-methylpentene-1, and octene, or with other monomeric materials, for example, methyl methacrylate, methyl acrylate, butyl acrylate, acrylonitrile, vinyl acetate, and styrene.

Irrespective of the polymerisation or copolymerisation technique employed, polymerisation or copolymerisation is typically carried out under conditions that substantially exclude oxygen, water, and other materials that act as catalyst poisons. Also, polymerisation or copolymerisation can be carried out in the presence of additives to control polymer or copolymer molecular weights.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of transition metal complex in the produced polymer can be very small.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts. In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials. Most preferably the catalyst system is supported on the support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer-product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent. The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure; for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. Such a process may be referred to as condensed mode and it is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

Homopolymerisation of ethylene with the catalysts of the invention may produce so-called "high density" grades of polyethylene. These polymers have relatively high stiffness and are useful for making articles where inherent rigidity is required. Copolymerisation of ethylene with higher 1-olefins (eg butene, hexene or octene) can provide a wide variety of copolymers differing in density and in other important physical properties. Particularly important copolymers made by copolymerising ethylene with higher 1-olefins with the catalysts of the invention are the copolymers having a density in the range of 0.91 to 0.93. These copolymers which are generally referred to in the art as linear low density polyethylene, are in many respects similar to the so called low density polyethylene produced by the high pressure free radical catalysed polymerisation of ethylene. Such polymers and copolymers are used extensively in the manufacture of flexible blown film.

Propylene polymers produced by the process of the invention include propylene homopolymer and copolymers of propylene with less than 50 mole % ethylene or other alpha-olefin such as butene-1, pentene-1,4-methylpentene-1, or hexene-1, or mixtures thereof. Propylene polymers also may include copolymers of propylene with minor amounts of a copolymerizable monomer. Typically, most useful are normally-solid polymers of propylene containing polypropylene crystallinity, random copolymers of propylene with up to about 10 wt. % ethylene, and impact copolymers containing up to about 20 wt. % ethylene or other alpha-olefin. Polypropylene homopolymers may contain a small amount (typically below 2 wt. %) of other monomers to the extent the properties of the homopolymer are not affected significantly.

Propylene polymers may be produced which are normally solid, predominantly isotactic, poly α-olefins. Levels of stereorandom by-products are sufficiently low so that useful products can be obtained without separation thereof. Typically, useful propylene homopolymers show polypropylene crystallinity and have isotactic indices above 90 and many times above 95. Copolymers typically will have lower isotactic indices, typically above 80–85.

Depending upon polymerisation conditions known in the art, propylene polymers with melt flow rates from below 1 to above 1000 may be produced in a reactor. For many applications, polypropylenes with a MFR from 2 to 100 are typical. Some uses such as for spunbonding may use a polymer with an MFR of 500 to 2000.

Peroxide compounds may be added to ethylene or propylene polymers. For ethylene based polymers, peroxides can be used to give cross-linking in the polymer. For the preparation of high MFR propylene polymers, peroxide compounds may be added during extrusion for controlled rheology to increase the melt flow rate of polymer. Peroxide acts to break long polymer chains and has the effect of both increasing MFR and narrowing the molecular weight distribution (Mw/Mn) or polydispersity. A typical reactor polypropylene powder with an MFR of 2 g/10 min. by controlled rheology treatment with peroxide in an extruder may form a polymer with an MFR of 20–40. By varying the type, amount of, and process conditions using, peroxide, the final polymer MFR may be controlled as known in the art.

Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thermoformed products, and the like. The polymers may be blown into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

Figure 1:
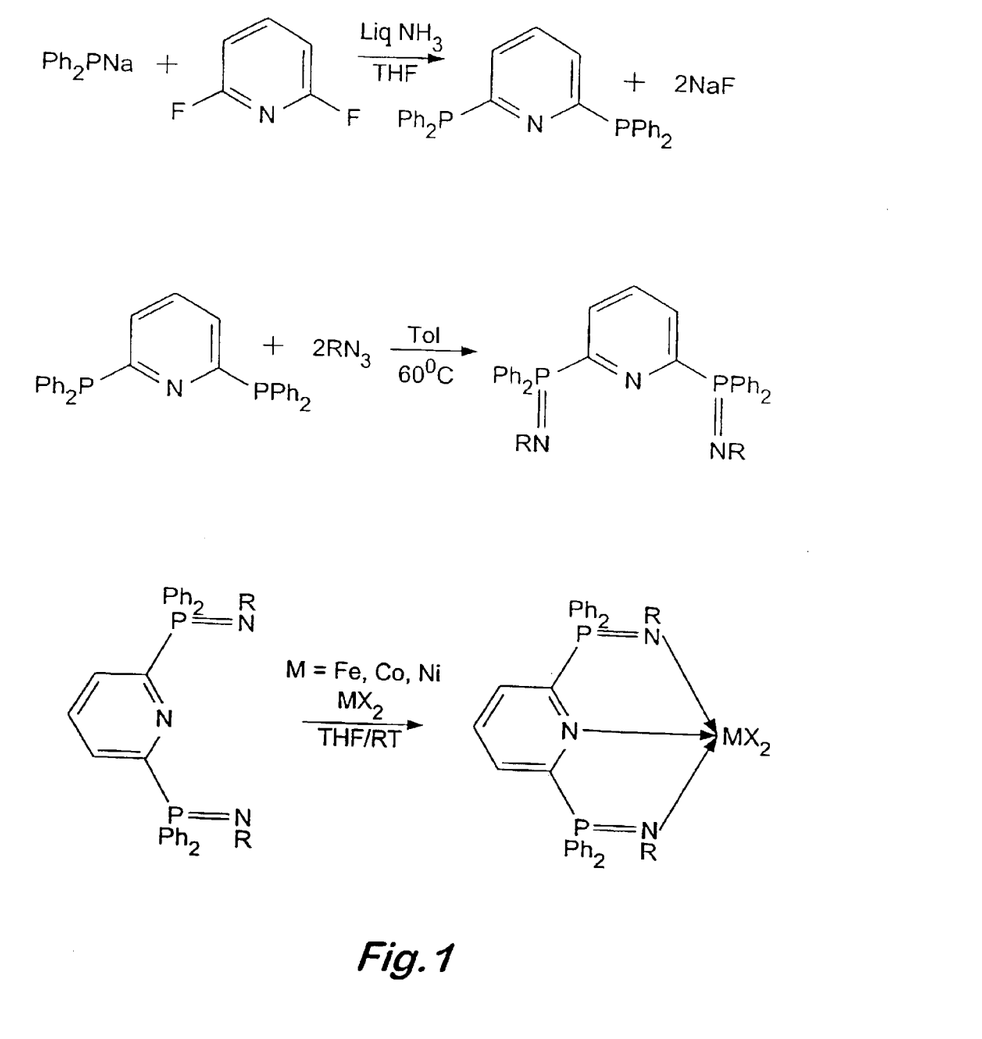
FIG. 1 is a reaction scheme for the preparation of complexes according to the present invention.

The present invention is illustrated in the following Examples. A reaction scheme for the preparation of complexes according to the present invention is shown in FIG. 1.

EXPERIMENTAL SECTION

General Considerations

All manipulations were performed under a nitrogen atmosphere. Solvents were distilled under $N_2$ over sodium benzophenone (THF), sodium (toluene), Na/K alloy[diethyl ether, light petroleum (bp 40–60° C.)], or $CaH_2$ (dichloromethane). NMR solvents were dried over activated molecular sieves and degassed through several freeze-thaw cycles. NMR spectra were recorded on Bruker ARX250 spectrometer. Chemical shifts are reported in ppm and referenced to residual solvent resonances ($^1H$, $^{13}C$). Chemical shifts are relative to external 85% $H_3PO_4$ for $^{31}P$ data. The anilines, triphenylphosphine and 2,6-difluoropyridine were purchased from Aldrich. $NiBr_2.DME$ was prepared according to literature procedure. (Inorganic Synthesis 13, 162). Anhydrous $CoCl_2$ was purchased from Aldrich, but to ensure total dryness was heated under vacuum before use.

EXAMPLE 1

Synthesis of Aniline Azides, $RN_3$(Chem. Ber. 1958, 91, 2330)

To a mixture of the 2,4,6-$Me_3$ $C_6H_2$ $NH_2$ (0.1 mol, 13.52 g) in 2M HCl and crushed ice was added sodium nitrite (0.107 mol, 7.38 g) dissolved in water. The solution was stirred for 20 min. Calcium carbonate was added to the diazonium salt, until the solution was neutralised. Sodium azide (0.116 mol, 7.54 g) in water was then added slowly and the solution stirred until no further effervescence was observed. The solution was extracted with 3×100 ml ether and the extracts combined and washed with sodium hydrogen carbonate solution before being dried over sodium sulphate. The solvent was removed under vacuum resulting in a red oil. The product was distilled as a yellow oil at 74–6° C./1 mmHg R=2,4,6-$Me_3$-$C_6H_2$ (Yield: 11.32 g, 0.07 mol, 70%) $^1H$ NMR (250 MHz, $CDCl_3$ 20° C.): δ6.9(s, 2H), 2.4(s, 6H), 2.2(s, 3H). $^{13}C$ NMR (250 MHz, $CDCl_3$ 20° C.): δ135(C—N), 134(m-$C_6H_5$), 131(o-$C_6H_5$), 129(p-$C_6H_5$), 20(2Me), 17(Me).

Where R=2,6-$^iPr_2(C_6H_3)$ the product was synthesized by the above procedure using 0.1 mol, 2,6-$^iPr_2C_6H_3NH_2$ 17.73 g. The product, a red oil, was not distilled due to danger of explosion and is used in 3–3 ½ excess in the following procedures. $^1H$ NMR (250 MHz, $CDCl_3$ 20° C.): δ7.3(t, 2H), 7.2(d, 1H), 3.4(m, 2H), 1.3(d, 12H).

EXAMPLE 2

Synthesis of 2,6-bis(diphenylphosphino)pyridine $PPh_2C_5H_3NPPh_2$ (Polyhedron 1990, 9, 1757)

To 1.0 mol sodium, approx. 1 l ammonia was condensed at −78° C. Triphenylphosphine (0.5 mol, 131 g) in 200 ml THF was added at −78° C. dropwise over one hour. Ammonium chloride (0.5 mol, 26.8 g) was added in small portions and the mixture allowed to stir for a further hour at low temperature. 2,6-difluoropyridine in 100 ml THF was added dropwise and the solution stirred for a further hour. Toluene (200 ml) was then added and the mixture allowed to warm to room temperature and stirred overnight. The solution which was dark red in colour was then refluxed until no further ammonia could be detected (ca. 1 hour). The solvent was removed under vacuum leaving a red oil to which 200 ml methanol was added resulting in a creamy precipitate. This was filtered under air through a glass sinter and then dried under vacuum. The product was isolated as a cream powder (103.8 g, 0.23 mol, 93%). $^1$H NMR (250 MHz, CDCl$_3$ 20° C.): δ7.25–7.36(m), 7.08(t), 7.05(t). $^{31}$P NMR: (250 MHz, CDCl$_3$): δ−5.0. Anal. Calcd for C$_{29}$H$_{23}$NP$_2$: C, 77.8; H. 5.14; N, 3.1; P, 13.8%. Found: C, 77.35; H, 5.01; N, 3.0; P, 13.7%. MS (EI): m/z 447 (M$^+$).

Synthesis of 2,6-Bis(aryliminophosphino)pyridines

EXAMPLE 3

2,6 C$_6$H$_3$N(PPh$_2$NR)$_2$, R=2,4,6 Me$_3$C$_6$H$_2$

To PPh$_2$C$_5$H$_3$NPPh$_2$, (0.014 mol, 6.26 g), prepared according to Example 2, in toluene at 60° C. 2.5 equivalents of 2,4,6-Me$_3$- C$_6$H$_2$N$_3$ (0.035 mol, 5.64 g) were added dropwise slowly and the solution stirred for 4 h at this temperature. The solvent was then removed under vacuum resulting in a brown oil, which was washed three times with ca. 100 ml of petrol leaving a cream solid which was dried under vacuum. C$_{47}$H$_{45}$N$_3$P$_2$, (Yield: 7.8 g, 0.01 mols, 78%) $^1$H NMR (250 MHz, CDCl$_3$ 20° C.): δ8.39(m), 7.89(m), 7.29–7.42(m), 7.11–7.42(m), 6.98(s, br), 2.14(s, 6H), 1.90 (s, 12H). $^{31}$P NMR: (250 MHz, CDCl$_3$): δ−13.8. Anal. Calcd for C$_{47}$H$_{45}$N$_3$P$_2$: C, 79.1; H. 6.3; N, 5.9; P, 8.7%. Found: C, 79.95; H, 6.26; N, 5.8; P, 8.6%. MS (EI): m/z 713 (M$^+$).

EXAMPLE 4

2,6 C$_6$H$_3$N(PPh$_2$NR)$_2$, R=2,6 $^i$Pr$_2$—C$_6$H$_3$

For R=2,6 $^i$Pr$_2$—C$_6$H$_3$, the product was synthesized by the above procedure using PPh$_2$C$_5$H$_3$NPPh$_2$ (8.1 mmol, 3.65 g) and 3.5 equivalents of $^i$Pr$_2$—C$_5$H$_3$N$_3$ (28.35 mmol, 5.78 g).

C$_{53}$H$_{57}$N$_3$P$_2$, (Yield: 3.4 g, 4 mmol, 54%) $^1$H NMR (250 MHz, CDCl$_3$ 20° C.): δ8.40(m), 7.97(m), 7.30–7.44(m), 7.15–7.25(m), 6.96(d), 6.84(d), 6.81(t), 3.24(m, 4H), 0.86(d, 24H). $^{31}$P NMR: (250 MHz, CDCl$_3$): δ−13. Anal. Calcd for C$_{47}$H$_{45}$N$_3$P$_2$: C, 79.6; H, 7.1; N, 5.2; P, 7.7%. Found: C, 77.35; H, 7.05; N, 4.9; P, 7.45%. MS (EI): m/z 797 (M$^+$).

Synthesis of MLX$_2$ Compounds (L=Ligand)

EXAMPLE 5

Ni{2,6 C$_5$H$_3$N(PPh$_2$NR)$_2$}Br$_2$, R=2,6 $^i$Pr$_2$—C$_6$H$_3$

To NiBr$_2$.DME (0.8 m mol, 0.248 g) in THF, a slight excess of L (2,6 C$_6$H$_3$N(PPh$_2$NR)$_2$, R=2,6 $^i$Pr$_2$—C$_6$H$_3$, prepared in Example 4) (0.85 m mol, 0.68 g) in THF was added at room temperature and an immediate colour change was noticed and the solution stirred overnight. The solvent was removed under vacuum the resulting solids were washed with petrol and then crystallized from CH$_2$Cl$_2$. The product was isolated as an olive green powder. (Yield: 89%, 0.73 g, 0.71 m mol). MS (FAB) m/z 936 (MLX$^+$).

EXAMPLE 6

Ni{2,6-C$_5$H$_3$N(PPh$_2$NR)$_2$}Br$_2$, R=2,4,6 Me$_3$-C$_6$H$_2$

This was synthesized by the above procedure using NiBr$_2$.DME (0.7 mol, 0.5 g) and L (2,6 C$_6$H$_3$N(PPh$_2$NR)$_2$, R=2,4,6 Me$_3$C$_6$H$_2$ prepared in Example 3, 0.75 m mol, 0.53 g). The product was obtained as an olive green powder. (Yield: 70%, 0.49 m mol, 0.46 g). MS (FAB) m/z 936 (MLX$^+$).

EXAMPLE 7

Co{2,6 C$_5$H$_3$N(PPh$_2$NR)$_2$}Cl$_2$ R=2,6 $^i$Pr$_2$—C$_6$H$_3$

This was synthesized by the above procedure using CoCl$_2$ (0.7 m mol, 0.091 g) and L (2,6 C$_6$H$_3$N(PPh$_2$NR)$_2$, R=2,6 $^i$Pr$_2$—C$_6$H$_3$, prepared in Example 4, 0.75 m mol, 0.63 g). The product was obtained as an olive green powder. (Yield: 74%, 0.56 m mol, 0.52 g). MS (FAB) m/z 892 (MLX$^+$).

EXAMPLE 8

Co{2,6—C$_5$H$_3$N(PPh$_2$NR)$_2$}Cl$_2$, R=2,4,6 Me$_3$-C$_6$H$_2$

This was synthesized by the above procedure using CoCl$_2$ (0.7 m mol, 0.09 g) and L (2,6 C$_6$H$_3$N(PPh$_2$NR)$_2$, R=2,4, 6Me$_3$C$_6$H$_2$ prepared in Example 3, 0.75 m mol, 0.53 g). The product was obtained as a green powder. (Yield: 75%, 0.53 mol, 0.44 g) MS (FAB) m/z 807 (MLX$^+$).

EXAMPLE 9

Fe{2,6 C$_5$H$_3$N(PPh$_2$NR)$_2$}Br$_2$, R=2,4,6 Me$_3$-C$_6$H$_2$

To a mixture of FeBr$_2$ (0.8 m mol, 0.212 g) and L (2,6 C$_6$H$_3$N(PPh$_2$NR)$_2$, R=2,4,6Me$_3$C$_6$H$_2$ prepared in Example 3, 0.98 m mol, 0.7 g) was added 40 ml of THF at room temperature. The colour slowly changed from orange to orange-red and the solution was stirred overnight. After filtration, the solvent of the filtrate was removed under vacuum and the resulting residue washed with toluene. The product was dried to give an olive green powder. (Yield: 56%, 0.51 g,). FDMS m/z 929 (MLX$_2^+$), 850 (MLX$^+$).

EXAMPLE 10

Fe{2,6 C$_5$H$_3$N(PPh$_2$NR)$_2$}Br$_2$, R=2,6 $^i$Pr$_2$—C$_6$H$_3$

The complex was prepared in analogy to above from FeBr$_2$ and L (2,6 C$_6$H$_3$N(PPh$_2$NR)$_2$, R=2,6 $^i$Pr$_2$—C$_6$H$_3$) prepared in Example 4.

Synthesis of Disphosphine Di-imines (Phosphorus, Sulfur and Silicon, 1990, 47, 401)

EXAMPLE 11

RNPPh$_2$CH$_2$PPh$_2$NR (R=phenyl)

To dppm (diphenylphopshinomethane), (0.05 mol, 19.59 g) in toluene at 60° C. 2.5 equivalents of PhN$_3$(0.125 mol, 14.9 g) was added dropwise slowly and the solution stirred for 4 h at this temperature. The solvent was then removed in vacuo resulting in an oil, which was washed with petrol three times leaving a cream solid. The solid was dried under vacuum. (Yield: 25.4 g, 0.045 mol, 90%). $^1$H NMR (250 MH$_z$,CDCl$_3$ 20° C.): δ (ppm): 7.70–7.75(m, 6H), 7.33–7.45 (m, 12H), 7.00–7.06(m, 4H), 6.60–6.71(m, 8H), 3.74(t, $^2$J(P.H)=13.6 H$_z$). $^{31}$P{$^1$H} NMR: (250 MH$_z$, CDCl$_3$): δ0.0.

Anal. Calcd for $C_{29}H_{22}NP_2$: C, 78.4; H, 5.65; N, 4.95; P, 11.0%. Found: C, 77.7: H. 5.8; N, 4.85; P, 10.8%. MS(El): m/z 565 (M).

EXAMPLE 12

$RNPPh_2CH_2PPh_2NR$ (R=2,4,6-$Me_3C_6H_2$)

This was synthesized by the above procedure using dppm (0.035 mol, 13.49 g) and 2 equivalents of 2,4,6 $Me_3.C_6H_2N_3$ (0.07 mol, 11.32 g). (Yield: 17.9 g, 0.027 mol. 78%). $^1H$ NMR (250 $MH_z$, $CDCl_3$ 20° C.): 8 (ppm): 7.58–7.66(m, 8H), 7.30–7.33(m, 4H), 7.16–7.23(m, 8H), 6.71($_s$, 4H), 3.9(t, $^2J(P—H)$=14.4 Hz), 2.23(s, 6H), 1.95(s 12H) $^{31}P\{^1H\}$ NMR: (250 $MH_z$, $CDCl_3$): δ–15 ppm Anal. Calcd for $C_{43}H_{44}N_2P_2$: C, 79.3; H, 6.7; N, 4.2; P, 9.7%. Found: C, 79.3; H. 6.8; N, 4.3; P, 9.5%. MS (El): m/z 650 ($M^+$).

EXAMPLE 13

$RNPPh_2CH_2PPh_2NR$ (R=2,6 $^iPr_2$—$C_6H_2$)

This was synthesized by the above procedure using dppm (7.8 mmol, 3.0 g) and 3 equivalents of 2,6 $^iPr_2$—$C_6H_3N_3$ (0.023 mol, 4.67 g). (Yield: 4.6 g, 6.2 mmol, 80%). $^1H$ NMR (250 $MH_z$, $CDCl_3$ 20° C.): 8(ppm): 7.46–7.54(m), 7.27–7.30 (m), 7.13–7.19(m), 6.93(s), 6.91(s), 3.91(t, $^2J(P—H)$ 15.2 $H_z$, 2H), 3.17(m, 4H), 0.88(d, 24H). $^{31}P$ NMR: (250 MHz, $CDCl_3$): δ–16 ppm Anal. Calcd for $C_{49}H_{56}N_2P_2$: $C_{49}H_{56}N_2P_2$: C, 80.0, H., 7.6; N, 3.8; Found: C, 78.9; H, 7.45; N, 3.55; P, 7.85% MS(El): m/z 733 ($M^+$).

Synthesis of $MLX_2$ Compounds (L=Lipand)

EXAMPLE 14

$Ni(RNPPh_2 CH_2PPh_2NR)Br_2$ R=Ph

To $NiBr_2DME$ (1.77 mmol, 0.55 g) in THF, a slight excess of L ($RNPPh_2CH_2PPh_2NR$ (R=phenyl), prepared in Example 11, 1.77 mmol, 1.0 g) in THF was added at room temperature and immediate colour change was noticed and the solution stirred overnight. This resulted in a slightly coloured solution and green precipitate. The THF was filtered off and the solid dried under vacuum. The product was isolated as a green powder. (Yield: 88%, 1.22 g, 1.55 mmol). MS(FAB) m/z 905 (MLX).

EXAMPLE 15

$Ni\{RNPPh_2CH_2PPh_2NR\}Br_2$ R=2,4,6 $Me_3$-$C_6H_2$

This was synthesized by the above procedure using $NiBr_2DME$ (1.4 mmol, 0.44 g) and $RNPPh_2CH_2PPh_2NR$ (R=2,4,6-$Me_3C_6H_2$) (1.55 mmol, 1 g). The product was obtained as a green powder. (Yield: 90%, 1.09 g, 1.3 mmol). MS (FAB) m/z 789 MLX).

EXAMPLE 16

$Ni\{RNPPh_2CH_2PPh_2NR\}Br_2$ R=2,6 $^iPr_2$—$C_6H_3$

This was synthesized by the above procedure using $NiBr_2$ DME (0.71 mmol, 0.219 g) and $RNPPh_2CH_2PPh_2NR$ (R=2,6 $^iPr_2$—$C_6H_2$) (0.71 mmol, 0.51 g). The product was obtained as a green powder. (Yield: 95%, 0.67 mmol, 0.64 g). MS(FAB) m/z 936 (MLX) IR: 1436 $cm^1$(P=N).

EXAMPLE 17

$Co\{RNPPh_2CH_2PPh_2NR\}Cl_2$ R=Ph

This was synthesized by the above procedure using $CoCl_2$ (2.1 mmol, 0.27 g) and $RNPPh_2CH_2PPh_2NR$ (R=phenyl) (2.1 mmol, 1.18 g). The product was obtained as a blue powder. (Yield: 91%, 1.9 mmol, 1.46 g). MS (FAB) m/z 660 (MLX).

EXAMPLE 18

$Co\{RNPPh_2CH_2PPh_2NR\}Cl_2$, R=2,4,6 $Me_3C_6H_2$

This was synthesized by the above procedure using $CoCl_2$ (0.768 mmol, 0.1 g) and $RNPPh_2CH_2PPh_2NR$ (R=2,4,6-$Me_3C_6H_2$) (0.768 mmol, 0.50 g). The product was obtained as a blue powder. (Yield: 95%, 0.729 (MLX).

EXAMPLE 19

$Co\{RNPPh_2CH_2PPh_2NR\}Cl_2$ R=2,6$^1Pr_2$—$C_6H_3$

This was synthesized by the above procedure using $CoCl_2$ (0.68 mmol, 0.088 g) and $RNPPh_2CH_2PPh_2NR$ (R=2,6 $^iPr_2$—$C_6H_2$) (0.68 mmol, 0.5 g). The product was obtained as a blue-green powder. (Yield: 93%, 0.63 mmol 0.55 g). MS(FAB) m/z 827 (MLX) IR: 1436 $cm^1$(P=N).

EXAMPLE 20

$PCv_2C_6H_3NPCy_2$ (Cy=cyclohexyl)

To $Cy_2PH$ (5.0 g, 25 mmol) in THF (50 $cm^3$), $^nBuLi$ (15.8 $cm^3$, 25 mmol) was added dropwise at –78° C. The solution was stirred for 0.5 h at this temperature them warmed to room temperature and stirred for a further 2 h. Next, 2,6-difluoropyridine (1.14 $cm^3$, 12.5 mmol) in THF (50 $cm^3$) was added dropwise at –78° C. and the solution was allowed to stir for 0.5 h at this temp before refluxing the solution overnight. The solvent was removed in vacuo leaving a cream coloured solid to which (100 $cm^3$) of methanol was added giving an orange solution and cream solid. The solution was filtered in air and the filtrate washed with petrol and dried under vacuum. (3.79 g, 8.0 mmol, 65%). $^1H$ NMR ($CDCl_3$ 20° C.): δ7.36(m, 3H, py), 2.14–0.90 (m, 44H, Cy). $^{31}P$ NMR ($CDCl_3$, 20 C): δ9.9. $^{13}C$ NMR ($CDCl_3$ 20° C.): δ161.3 (d,d, py-$C_i$, J=14.6, 2.2), 133.1 (t, py-$C_p$, J=11.1), 131.5 (d, py-$C_m$, J=42.3), 32.5 (d, i-Cy, J=10.2), 29.8 (d, o-Cy, J=14.7), 29.4 (d, m-Cy, J=8.3), 27.4 (d, o-Cy, J=11.9), 27.0 (d, m-Cy, J=8.3), 26.5 (Ph, p-Cy).

EXAMPLE 21

2,6 $C_5H_3N(PCy_2NR)_2$, R=2,6 $^iPr_2$—$C_6H_3$

A toluene solution of $PCy_2C_6H_3NPCy_2$ (2.0 g, 4.2 mmol) was heated to 60° C. and treated dropwise with 2.5 equivalents of (2,6-diisopropyl) phenyl azide (2.15 g, 11 mmol) and then stirred for 0.5 hr. at this temperature. The solvent was removed under vacuum resulting in a brown oil which was washd three times with petrol (approx. 100 ml) leaving 2,6 $C_5H_3N(PCy_2NR)_2$, R=2,6 $^iPr_2$—$C_6H_3$ (2.4 g, 2.9 mmol, 70%). $^1H$ NMR ($CDCl_3$ 20° C.): δ8.07 (m, 2H, py-m-H), 7.81 (m, 1H, py-p-H), 6.95 (d, 4H, m-Isityl, J=7.1), 6.73 (t, 2H, p-Isityl, J=7.1), 3.20 (sept, 4H, $^iPr$—H, J=6.7), 2.44 (brm, 4H, Cy), 2.30 (brm, 4H, Cy), 1.78 (brm, 4H, Cy), 1.65 (brm, 14H, Cy), 1.23 (brm, 18H, Cy), 1.16 (d, 24H, $^iPr$—Me, J=6.7); $^{13}C$ NMR ($CDCl_3$ 20° C.): δ156.5 (d,d, py-$C_i$, $J_{CP}$=108.1, 15.2), 145.6 (s, $C_i$-Isityl-Ph), 141.9 (d, $C_o$-Isityl-Ph, $J_{CP}$=5.5) 134.7 (t, py-$C_p$, $J_{CP}$=7.5), 130.3 (d,d, py-$C_m$, $J_{CP}$=15.8, 2.8), 122.9 (s, $C_m$-Isityl-Ph), 118.5 (s, $C_p$-Isityl-Ph), 37.1 (d, Cy-$C_i$, $J_{CP}$=66.0), 29.1 ($^iPr$—CH), 27.4 (d, Cy, $J_{CP}$=4.2), 27.3 (d, Cy, $J_{CP}$=5.2), 27.1 (s, Cy), 26.5 (s, Cy), 26.2 (s, Cy); $^{31}P$ NMR: ($CDCl_3$): δ1.2. Anal. Calc for $C_{53}H_{81}N_3P_2$: C, 77.4; H, 9.9; N, 5.1; P, 7.5%. Found: C, 77.1; H. 9.7; N, 4.9; P, 7.5%.

EXAMPLE 22

Ni{2,6 C$_6$H$_3$N(PCy$_2$NR)$_2$}Br$_2$ R=2,6 $^i$Pr$_2$—C$_6$H$_3$

In a glove box NiBr$_2$.DME (0.24 g, 0.77 mmol) and 2,6 C$_5$H$_3$N(PCy$_2$NR)$_2$, R=2,6 $^i$Pr$_2$—C$_6$H$_3$ (0.63 g, 0.77 mmol) was weighed into a Schlenk tube with Youngs tap and attached to a vacuum line. Next THF (30 cm$^3$) were added and the mixture stirred in a closed system for 24 hrs at ambient temperature. The solvent was removed and the residue was washed with light petroleum and recrystallised from dichloromethane as a olive green powder (0.63 g, 0.60 mmol, 79%).

EXAMPLE 23

Co{2,6 C$_6$H$_3$N(PCy$_2$NR)$_2$}Br$_2$ R=2,6 $^i$Pr$_2$—C$_6$H$_3$

This was synthesised by the above procedure using CoCl$_2$ (0.14 g, 1.09 mmol) and 2,6 C$_5$H$_3$N(PCy$_2$NR)$_2$, R=2,6 $^i$Pr$_2$—C$_6$H$_3$ (0.63 g, 0.77 mmol). The product was obtained as a green powder. (0.72 g, 0.76 mmol, 72%,).

Catalyst Evaluation

Catalyst evaluation was carried out in a stirred 1 L autoclave operated in slurry mode using isobutane solvent. Agitation was carried out using a paddle stirrer and heat exchange carried out via the autoclave jacket.

Before catalyst evaluation the autoclave was cleaned, assembled and baked out by heating to 95° C. and purging the vessel with dry O$_2$ free N$_2$ for 1 hour. The vessel was then cooled down under N$_2$ to about the polymerisation temperature.

Data logging was started and the catalyst injection system purged with N$_2$.

Catalyst solutions were then injected into the autoclave using N$_2$ overpressured. Polymerisation was allowed to continue, ethylene being taken up on demand. After the test period the ethylene gas was isolated, the reactor cooled, depressurised and the polymer unloaded.

The results are given below in the Table.

The complexes used for polymerisation were as follows:

| EXAMPLE | COMPLEX |
|---------|---------|
| A | Fe{2,6.C$_5$H$_3$N(PPh$_2$NR)$_2$}Br$_2$ R=2,6$^i$Pr$_2$C$_6$H$_3$ |
| B | Co{2,6-C$_5$H$_3$N(PPh$_2$NR)$_2$}Cl$_2$ R=2,4,6-Me$_3$C$_6$H$_2$ |
| C–G | Co{RNPPh$_2$CH$_2$PPh$_2$NR}Cl$_2$ R=2,6$^i$Pr$_2$C$_6$H$_3$ |

What is claimed is:

1. A polymerization catalyst comprising
   (1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M;

R is independently selected from hydrogen, halogen, hydrocarbyl, substituted hydrocarbyl, heterohydrocarbyl or substituted heterohydrocarbyl;

Z is a bridging group comprising a donor atom of N, P or S or alternatively is a neutral group comprising a C$_{1-4}$ alkylene group, a silyl group or a germyl group; and n=an integer to satisfy the valency of M, (2) an activating quantity of an activator compound, and
   (3) a support.

2. A polymerization catalyst comprising
   (1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; Z is a bridging group comprising a donor atom of N, P or S or alternatively is a neutral group comprising a C$_{1-4}$ alkylene group, a silyl group or a germyl group;

TABLE 1

| Example | Catalyst used/mg | Run T/ oC | Run P bar | Run time/h | Yield of PE/g | Activity g/gMetal/hr/b | Activity g/mmol/hr/bar | Mn/ g/mol | Mw/ g/mol | Mw/Mn | Mpk/ g/mol | MAO:cat. ratio |
|---------|------------------|-----------|-----------|------------|---------------|------------------------|------------------------|-----------|-----------|-------|------------|----------------|
| A | 4.9 | 50 | 10 | 4.50 | 1.20 | 91 | 5 | 168000 | 392000 | 2.3 | 379000 | 1040 |
| B | 7.4 | 50 | 10 | 1.08 | trace polymer | — | — | 112000 | 231000 | 2.1 | 177000 | 570 |
| C | 5.8 | 30 | 10 | 1.00 | 1.80 | 463 | 27 | 76000 | 369000 | 4.9 | 278000 | 673 |
| D | 6.2 | 50 | 10 | 0.67 | 6.30 | 2273 | 132 | 48000 | 396000 | 8.2 | 68000 | 574 |
| E | 5.1 | 80 | 10 | 1.33 | 0.62 | 136 | 8 | 90000 | 153000 | 1.7 | 98000 | 765 |
| F | 8.6 | 30 | 10 | 1.0 | 1.0 | 210 | 12 | | | | | 905 |
| G | 6.5 | 80 | 10 | 1.0 | 1.0 | 229 | 13 | | | | | 1000 |

$R^1$–$R^{14}$ are independently selected from hydrogen, halogen, hydrocarbyl, substituted hydrocarbyl, heterohydrocarbyl or substituted heterohydrocarbyl; and n = an integer to satisfy the valency of M, (2) an activating quantity of an activator compound, and
(3) a support.

3. A polymerization catalyst comprising
(1) a complex having the formula wherein M is Fe[II], Fe[III], Ni[II], Co[I], Co[II], Co[III], Mn[I], Mn[II], Mn[III], Mn[IV], Ru[II], Ru[III], Ru[IV], Pd[II], V[III], V[IV] or V[V];

X represents an atom or group covalently or ionically bonded to the transition metal M;

Z is a bridging group comprising a donor atom of N, P or S or alternatively is a neutral group comprising a $C_{1-4}$ alkylene group, a silyl group or a germyl group;

$R^1$–$R^{14}$ are independently selected from hydrogen, halogen, hydrocarbyl, substituted hydrocarbyl, heterohydrocarbyl, or substituted heterohydrocarbyl, and at least one of $R^1$–$R^{10}$ contains two or more carbon atoms; and n = an integer to satisfy the valency of M, and (2) an activating quantity of an activator compound, and
(3) a support.

4. The polymerization catalyst of claim 2 or 3 wherein $R^{11}$–$R^{14}$ are phenyl, alkyl or cycloalkyl.

5. The polymerization catalyst of claim 1, 2, or 3 wherein the bridging group Z is -$CH_2$- or a donor atom N.

6. The polymerization catalyst of claim 2 or 3 having the formula:

wherein R is hydrogen or hydrocarbyl.

7. The polymerization catalyst of claim 1, 2, or 3 wherein the metal M is Fe or Co.

8. The polymerization catalyst of claim 1, 2, or 3 wherein the Group X is chloride.

9. The polymerization catalyst of claim 1, 2, or 3 wherein the activator compound is an organoaluminum compound or a hydrocarbylboron compound.

10. The polymerization catalyst of claim 1, 2, or 3 further comprising a neutral Lewis base.

11. The polymerization catalyst of claim 1, 2 or 3 wherein the support is silica, alumina, or zirconia or is a polymer or prepolymer.

12. The polymerization catalyst of claim 1, 2, or 3 further comprising a catalyst suitable for the polymerization of olefins selected from the group consisting of Ziegler-Natta catalysts, metallocene-based catalysts, monocyclopentadienyl- and constrained geometry based catalysts, or heat activated supported chromium oxide catalysts.

13. A polymerization catalyst comprising (1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M;

R is independently selected from hydrogen, halogen, hydrocarbyl, substituted hydrocarbyl, heterohydrocarbyl or substituted heterohydrocarbyl;

Z is a bridging group comprising a donor atom of N, P or S or alternatively is a neutral group comprising a $C_{1-4}$ alkylene group, a silyl group or a germyl group; and n = an integer to satisfy the valency of M, (2) an activating quantity of an activator compound, and

(3) a catalyst suitable for the polymerization of olefins selected from the group consisting of Ziegler-Natta catalysts, metallocene-based catalysts, monocyclopentadienyl- or constrained geometry based catalysts, and heat activated support chromium oxide catalysts.

14. A polymerization catalyst comprising
(1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; Z is a bridging group comprising a donor atom of N, P or S or alternatively is a neutral group comprising a $C_{1-4}$ alkylene group, a silyl group or a germyl group;
$R^1$–$R^{14}$ are independently selected from hydrogen, halogen, hydrocarbyl, substituted hydrocarbyl, heterohydrocarbyl or substituted heterohydrocarbyl; and
n = an integer to satisfy the valency of M,
  (2) an activating quantity of an activator compound, and
  (3) a catalyst suitable for the polymerization of olefins selected from the group consisting of Ziegler-Natta catalysts, metallocene-based catalysts, monocyclopentadienyl- or constrained geometry based catalysts, and heat activated supported chromium oxide catalysts.

15. A polymerization catalyst comprising
(1) a complex having the formula wherein M is Fe[II], Fe[III], Ni[II], Co[I], Co[II], Co[III], Mn[I], Mn[II], Mn[III], Mn[IV], Ru[II], Ru[III], Ru[IV], Pd[II], V[III], V[IV] or V[V];
X represents an atom or group covalently or ionically bonded to the transition metal M;
Z is a bridging group comprising a donor atom of N, P or S or alternatively is a neutral group comprising a $C_{1-4}$ alkylene group, a silyl group or a germyl group;
$R^1$–$R^{14}$ are independently selected from hydrogen, halogen, hydrocarbyl, substituted hydrocarbyl, heterohydrocarbyl, or substituted heterohydrocarbyl, and at least one of $R^1$–$R^{10}$ contains two or more carbon atoms; and
n = an integer to satisfy the valency of M,
  (2) an activating quantity of an activator compound, and
  (3) a catalyst suitable for the polymerization of olefins selected from the group consisting of Ziegler-Natta catalysts, metallocene-based catalysts, monocyclopentadienyl- or constrained geometry based catalysts, and heat activated supported chromium oxide catalysts.

16. The polymerization catalyst of claim 14 or 15 wherein $R^{11}$–$R^{14}$ are phenyl, alkyl, or cycloalkyl.

17. The polymerization catalyst of claim 13, 14, or 15 wherein the bridging group Z is -$CH_2$- or a donor atom N.

18. The polymerization catalyst of claim 14 or 15 having the formula:

wherein R is hydrogen or hydrocarbyl.

19. The polymerization catalyst of claim 13, 14, or 15 wherein the metal M is Fe or Co.

20. The polymerization catalyst of claim 13, 14, or 15 wherein the Group X is chloride.

21. The polymerization catalyst of claim 13, 14, or 15 wherein the activator compound is an organoaluminum compound or a hydrocarbylboron compound.

22. The polymerization catalyst of claim 13, 14, or 15 further comprising a neutral Lewis base.

23. The polymerization catalyst of claim 13, 14, or 15 further comprising a support.

24. The polymerization catalyst of claim 23 wherein the support is silica, alumina, or zirconia or is a polymer or prepolymer.

25. A polymerization catalyst comprising
(1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M;
R is independently selected from hydrogen, halogen, hydrocarbyl, substituted hydrocarbyl, heterohydrocarbyl or substituted heterohydrocarbyl;

Z is -CH$_2$-; and
n = an integer to satisfy the valency of M, and
(2) an activating quantity of an activator compound.

26. A polymerization catalyst comprising
(1) a transition metal complex having the formula:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M;
Z is -CH$_2$-;
R$^1$–R$^{14}$ are independently selected from hydrogen, halogen, hydrocarbyl, substituted hydrocarbyl, heterohydrocarbyl or substituted heterohydrocarbyl; and
n = an integer to satisfy the valency of M, and
(2) an activating quantity of an activator compound.

27. A polymerization catalyst comprising
(1) a complex having the formula wherein M is Fe[II], Fe[III], Ni[II], Co[I], Co[II], Co[III], Mn[I], Mn[II], Mn[III], Mn[IV], Ru[II], Ru[III], Ru[IV], Pd[II], V[III], V[IV] or V[V];
X represents an atom or group covalently or ionically bonded to the transition metal M;

Z is -CH$_2$-;

R$^1$–R$^{14}$ are independently selected from hydrogen, halogen, hydrocarbyl, substituted hydrocarbyl, heterohydrocarbyl, or substituted heterohydrocarbyl, and at least one of R$^1$–R$^{10}$ contains two or more carbon atoms; and n = an integer to satisfy the valency of M, and (2) an activating quantity of an activator compound.

28. The polymerization catalyst of claim 26 or 27 wherein R$^{11}$–R$^{14}$ are phenyl, alkyl, or cycloalkyl.

29. The polymerization catalyst of claim 25, 26, or 27 wherein the metal M is Fe or Co.

30. The polymerization catalyst of claim 25, 26, or 27 wherein the Group X is chloride.

31. The polymerization catalyst of claim 25, 26, or 27 wherein the activator compound is an organoaluminum compound or a hydrocarbylboron compound.

32. The polymerization catalyst of claim 25, 26, or 27 further comprising a neutral Lewis base.

33. The polymerization catalyst of claim 25, 26, or 27 further comprising a support.

34. The polymerization catalyst of claim 33 wherein the support is silica, alumina, or zirconia or is a polymer or prepolymer.

35. The polymerization catalyst of claim 25, 26, or 27 further comprising a catalyst suitable for the polymerization of olefins selected from the group consisting of Ziegler-Natta catalysts, metallocene-based catalysts, monocyclopentadienyl- or constrained geometry based catalysts, and heat activated supported chromium oxide catalysts.

36. A process for the polymerization or copolymerization of olefins comprising contacting a monomeric olefin under polymerization conditions with a catalyst as defined in claim 1, 2, 3, 13, 14, 15, 25, 26, or 27.

37. The process of claim 36 wherein the polymerization conditions are solution phase, slurry phase, or gas phase.

38. The process of claim 37 wherein the polymerization is conducted under gas phase fluidized bed conditions.

39. The process of claim 38 wherein the polymerization is conducted under condensed mode.

40. The process of claim 36 wherein hydrogen is used to control the average molecular weight of the polymer.

* * * * *

UNITED STATES PATENT AND TRADEMARK OFFICE
CERTIFICATE OF CORRECTION

PATENT NO. : 6,762,258 B2
DATED : July 14, 2004
INVENTOR(S) : Manfred Bochmann et al.

It is certified that error appears in the above-identified patent and that said Letters Patent is hereby corrected as shown below:

Column 19,
Line 28, "orV[V];" should read -- or V[V]; --.

Column 20,
Line 16, "1, 2 or 3" should read -- 1, 2, or 3 --.
Line 66, "support" should read -- supported --.

Signed and Sealed this

Eighth Day of March, 2005

JON W. DUDAS
*Director of the United States Patent and Trademark Office*